United States Patent
Nozaki et al.

(10) Patent No.: US 7,037,673 B2
(45) Date of Patent: May 2, 2006

(54) DIPEPTIDE PRODUCTION METHOD, L-AMINO ACID AMIDE HYDROLASE USED THEREIN, AND PRODUCTION METHOD OF L-AMINO ACID AMIDE HYDROLASE

(75) Inventors: Hiroyuki Nozaki, Kanagawa (JP); Ikuo Kira, Kanagawa (JP); Sonoko Suzuki, Kanagawa (JP); Kenzo Yokozeki, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 206 days.

(21) Appl. No.: 10/481,087

(22) PCT Filed: Jul. 26, 2002

(86) PCT No.: PCT/JP02/07633

§ 371 (c)(1),
(2), (4) Date: Dec. 17, 2003

(87) PCT Pub. No.: WO03/010187

PCT Pub. Date: Feb. 6, 2003

(65) Prior Publication Data

US 2005/0054067 A1  Mar. 10, 2005

(30) Foreign Application Priority Data

Jul. 26, 2001 (JP) ............... 2001-226568
Oct. 5, 2001 (JP) ............... 2001-310547

(51) Int. Cl.
*C12P 21/00* (2006.01)
*C12N 9/58* (2006.01)

(52) U.S. Cl. .................... 435/68.1; 435/223

(58) Field of Classification Search ............... 435/68.1, 435/223

See application file for complete search history.

(56) References Cited

FOREIGN PATENT DOCUMENTS

EP      0278 787      8/1988

(Continued)

OTHER PUBLICATIONS

A. Schwarz, et al., "A two-step enzymetic synthesis of dipeptides". Biotechnology and Bioengineering. vol. 39, No. 2, pp. 132-140, Jan. 20, 1992.

(Continued)

*Primary Examiner*—Charles L. Patterson, Jr.
(74) *Attorney, Agent, or Firm*—Oblon, Spivak, McClelland, Maier & Neustadt, P.C.

(57) ABSTRACT

A process for industrially advantageously producing a dipeptide via a convenient pathway starting with less expensive and easily available materials is provided. A dipeptide is produced from an L-amino acid amide and an L-amino acid by using a culture of a microbe capable of synthesizing the dipeptide from the L-amino acid amide and the L-amino acid, microbial cells separated from the culture or a treated microbial cell product from the microbe. An L-amino acid amide hydrolase is obtained from a microbe belonging to the genus *erwinia*, genus *Rhodococcus*, genus *Chryseobacterium*, genus *Micrococcus*, genus *Cryptococcus*, genus *Trichosporion*, genus *Rhodosporidium*, genus *Sporobolomyces*, genus *Tremela*, genus *Torulaspora*, genus *Sterigmatomyces* or genus *Rhodotorula*. The hydrolase catalyzes a reaction that produces a dipeptide from an L-amino acid amide and an L-amino acid.

9 Claims, 3 Drawing Sheets

FOREIGN PATENT DOCUMENTS

| | | |
|---|---|---|
| EP | 1108790 | 6/2001 |
| JP | 53-92729 | 8/1978 |
| JP | 1-96194 | 4/1989 |
| JP | 6-234715 | 8/1994 |
| JP | 10-136992 | 5/1998 |
| WO | 90/01555 | 2/1990 |
| WO | 01/00842 | 1/2001 |

OTHER PUBLICATIONS

Shiro Akabori, et al., Bull. Chem. Soc. vol. 34, pp. 739, 1961.

Yasutsugu Shimonishi, et la., Bull. Chem. Soc. vol. 35, No. 12, pp. 1966-1970, 1962.

Yasutsugu Shimonishi, Bull. Chem. Soc. vol. 37, No. 2. pp. 200-203, 1962.

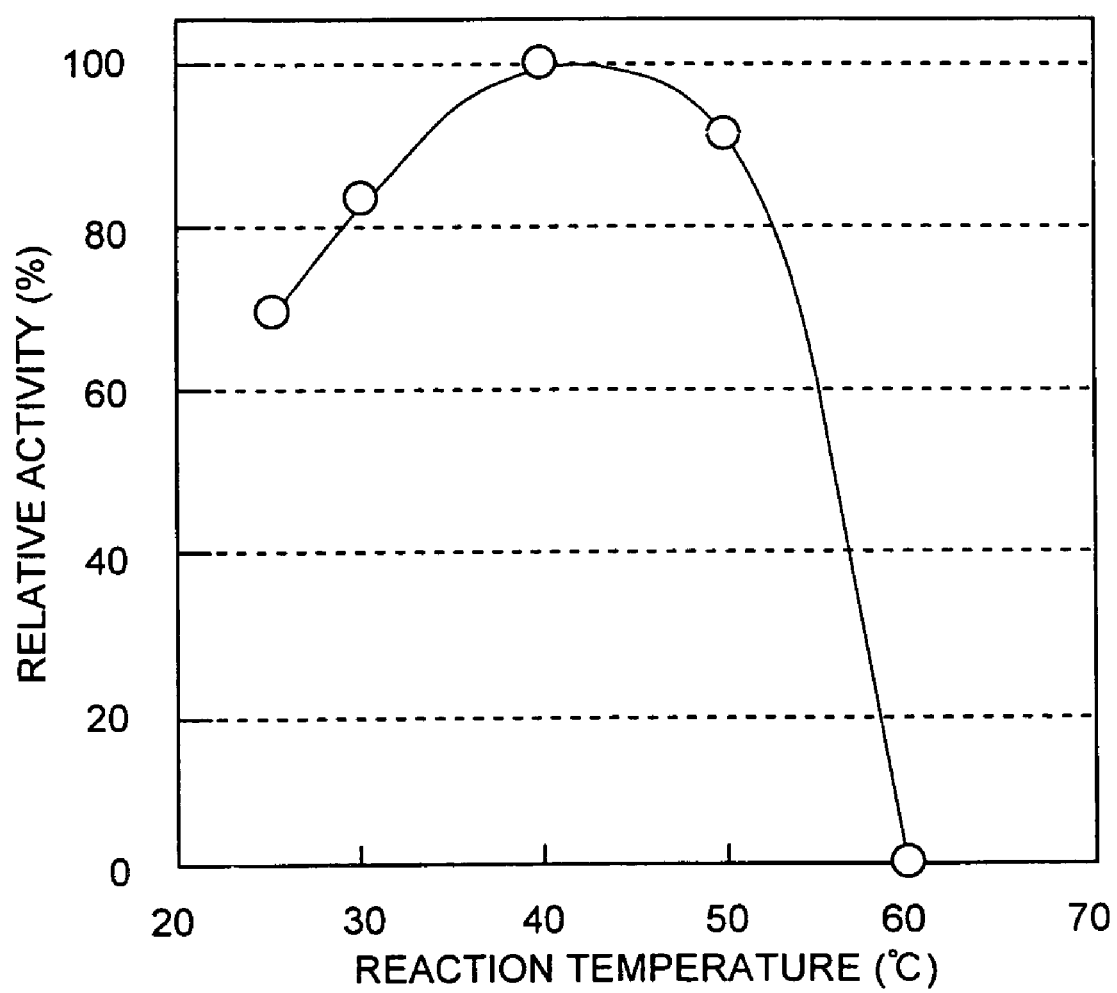

DIPEPTIDE PRODUCTION METHOD, L-AMINO ACID AMIDE HYDROLASE USED THEREIN, AND PRODUCTION METHOD OF L-AMINO ACID AMIDE HYDROLASE

CROSS-REFERENCE TO RELATED APPLICATIONS

The present application is a National Stage (371) of PCT/JP02/07633 filed on Jul. 26, 2002, which claims priority to JP 2001-226568, filed on Jul. 26, 2001, and to JP 2001-310547, filed on Oct. 5, 2001.

1. Technical Field

The present invention relates to a method for producing dipeptides easily and inexpensively without going through a complex synthesis method, and more particularly, to a method for producing dipeptides from an L-amino acid amide and an L-amino acid, to an L-amino acid amide hydrolase used in the method for producing dipeptides, and to a production method of the same.

2. Background Art

Dieptides are used in the field of pharmaceuticals and functional foods and various other fields. For example, L-alanyl-L-glutamine is useful as a component of serum-free media, and since it has higher stability and water-solubility than L-glutamine, it is used for fluid infusion.

Although chemical synthesis methods are conventionally known in the art as methods for producing dipeptides, those production methods are not necessarily easy. Known examples of such methods include a method that uses N-benzyloxycarbonylalanine (hereinafter, "Z-alanine") and protected L-glutamine (see Bull. Chem. Soc. Jpn., 34, 739 (1961), Bull. Chem. Soc. Jpn., 35, 1966 (1962)), a method that uses Z-alanine and protected L-glutamic acid-γ-methyl ester (see Bull. Chem. Soc. Jpn., 37, 200 (1964)), a method that uses a Z-alanine ester and unprotected glutamic acid (see Japanese Patent Application Laid-open Publication No. H1-96194), and a method that uses a 2-substituted-propionyl halide as a raw material to synthesize a dipeptide using an N-(2-substituted)-propionyl glutamine derivative as an intermediate (see Japanese Patent Application Laid-open Publication No. H6-234715).

However, since all of these methods require the introduction and elimination of protecting groups or the synthesis of an intermediate, they are not considered to be adequately satisfactory in terms of their industrial advantages.

In addition, known examples of methods for producing dipeptides using microbial enzyme system include a method that uses Z-aspartic acid and methyl ester of phenylalanine (see Japanese Patent Application Laid-open Publication No. S53-92729), and a method that uses aspartic acid amide and methyl ester of phenylalanine (see Japanese Patent Application Laid-open Publication No. H10-136992). Other known examples of methods for producing dipeptides by an enzymatic process are described in EPA 0278787 and WO 90/01555.

However, in all of these microbial enzyme systems, since it is necessary to use an amino acid having a protecting group for the starting substance, there is a need to develop a method for producing dipeptides that uses raw materials that are available comparatively inexpensively and easily, is industrially advantageous and employs a simple production pathway.

DISCLOSURE OF THE INVENTION

It is an object of the present invention to provide a method for producing dipeptides that uses comparatively inexpensive and easily available starting materials, is industrially advantageous and employs a simple production pathway.

As a result of conducting extensive research in consideration of the aforementioned object, the inventors of the present invention found that certain microbes have the ability to form dipeptides from comparatively inexpensive and easily available L-amino acid amides and L-amino acids, thereby having completed the present invention.

Namely, the present invention is as described below.

[1] A dipeptide production method comprising: producing a dipeptide from an L-amino acid amide and an L-amino acid using an enzyme or enzyme-containing substance having an L-amino acid amide hydrolase activity.

[2] The dipeptide production method according to [1] described above, wherein the enzyme or enzyme-containing substance is one or two or more types selected from the group consisting of a culture of microbes having an L-amino acid amide hydrolase activity, microbial cells separated from the culture, and a treated microbial cell product from the microbes.

[3] The dipeptide production method according to [2] described above, wherein the microbe belongs to the genus *Bacillus*, genus *Corynebacterium*, genus *Erwinia*, genus *Rhodococcus*, genus *Chryseobacterium*, genus *Micrococcus*, genus *Pseudomonas*, genus *Cryptococcus*, genus *Trichosporon*, genus *Rhodosporidium*, genus *Sporobolomyces*, genus *Tremela*, genus *Torulaspora*, genus *Sterigmatomyces* or genus *Rhodotorula*.

[4] The dipeptide production method according to [1] described above, wherein the enzyme is a protein (A) or (B):

(A) a protein having the amino acid sequence described in SEQ ID No.: 5 of the Sequence Listing, (B) a protein having an amino acid sequence that contains a substitution, deletion, insertion, addition or inversion of one or a plurality of amino acids in the amino acid sequence described in SEQ ID No.: 5 of the Sequence Listing, and having an L-amino acid amide hydrolase activity that catalyzes a reaction that produces a dipeptide from the L-amino acid amide and the L-amino acid;

[5] The dipeptide production method according to [1] described above, wherein the enzyme is a protein encoded by a DNA of (C):

(C) a DNA that hybridizes under stringent conditions with a polynucleotide that consists of a base sequence complementary to the base sequence of bases nos. 57 to 1295 described in SEQ ID No.: 4 of the Sequence Listing, and encodes a protein having an L-amino acid amide hydrolase activity that catalyzes a reaction that produces a dipeptide from the L-amino acid amide and the L-amino acid.

[6] The dipeptide production method according to [2], wherein the microbe is a microbe that has been transformed so as to be able to express the protein (A), (B) or (C):

(A) a protein having the amino acid sequence described in SEQ ID No.: 5 of the Sequence Listing, (B) a protein having an amino acid sequence that contains a substitution, deletion, insertion, addition or inversion of one or a plurality of amino acids in the amino acid sequence described in SEQ ID No.: 5 of the Sequence Listing, and having an L-amino acid amide hydrolase activity that catalyzes a reaction that produces a dipeptide from the L-amino acid amide and the L-amino acid, (C) a protein encoded by a DNA that hybridizes under stringent conditions with a polynucleotide that consists of a base sequence complementary to the base sequence of base nos. 57 to 1295 described in SEQ ID No.: 4 of the Sequence Listing, and encodes protein having an L-amino acid amide hydrolase activity that catalyzes a reaction that produces a dipeptide from the L-amino acid amide and the L-amino acid.

[7] The dipeptide production method according to any one of [1] to [6], wherein the L-amino acid amide is one or two or more types selected from the group consisting of L-alanine amide, glycine amide and L-aspartic acid-α-amide.

[8] The dipeptide production method according to any one of [1] to [7], wherein the L-amino acid is one or two or more types selected from the group consisting of L-glutamine, L-asparagine, glycine, L-alanine, L-valine, L-leucine, L-isoleucine, L-methionine, L-proline, L-phenylalanine, L-tryptophan, L-serine, L-threonine, L-tyrosine, L-lysine, L-arginine, L-histidine and L-glutamine.

[9] An L-amino acid amide hydrolase obtained from a microbe belonging to the genus *Erwinia*, genus *Rhodococcus*, genus *Chryseobacterium*, genus *Micrococcus*, genus *Cryptococcus*, genus *Trichosporon*, genus *Rhodosporidium*, genus *Sporobolomyces*, genus *Tremela*, genus *Torulaspora*, genus *Sterigmatomyces* or genus *Rhodotorula*, which catalyzes a reaction that produces a dipeptide from an L-amino acid amide and an L-amino acid.

[10] A production method of L-amino acid amide hydrolase, comprising: culturing a microbe belonging to the genus *Erwinia*, genus *Rhodococcus*, genus *Chryseobacterium*, genus *Micrococcus*, genus *Cryptococcus*, genus *Trichosporon*, genus *Rhodosporidium*, genus *Sporobolomyces*, genus *Tremela*, genus *Torulaspora*, genus *Sterigmatomyces* or genus *Rhodotorula* in a medium, and accumulating in the medium and/or cells an L-amino acid amide hydrolase that catalyzes a reaction that produces a dipeptide from an L-amino acid amide and an L-amino acid.

[11] A production method of L-amino acid amide hydrolase, comprising: culturing a microbe transformed so as to be able to express a protein (A), (B) or (C):

(A) a protein having the amino acid sequence described in SEQ ID No.: 5 of the Sequence Listing, (B) a protein having an amino acid sequence that contains a substitution, deletion, insertion, addition or inversion of one or a plurality of amino acids in the amino acid sequence described in SEQ ID No.: 5 of the Sequence Listing, and having an L-amino acid amide hydrolase activity that catalyzes a reaction that produces a dipeptide from the L-amino acid amide and the L-amino acid, (C) a protein encoded by a DNA that hybridizes under stringent conditions with a polynucleotide that consists of a base sequence complementary to the base sequence of bases nos. 57 to 1295 described in SEQ ID No.: 4 of the Sequence Listing, and encodes a protein having an L-amino acid amide hydrolase activity that catalyzes a reaction that produces a dipeptide from the L-amino acid amide and the L-amino acid, and accumulating in the medium and/or cells an L-amino acid amide hydrolase that catalyzes a reaction that produces a dipeptide from an L-amino acid amide and an L-amino acid.

BRIEF DESCRIPTION OF THE DRAWINGS

FIG. 3 is a graph of the optimum temperature curve of an L-amino acid amide hydrolase derived from *Corynebacterium glutamicum* ATCC 13286.

BEST MODE FOR CARRYING OUT THE INVENTION

Figure 1:
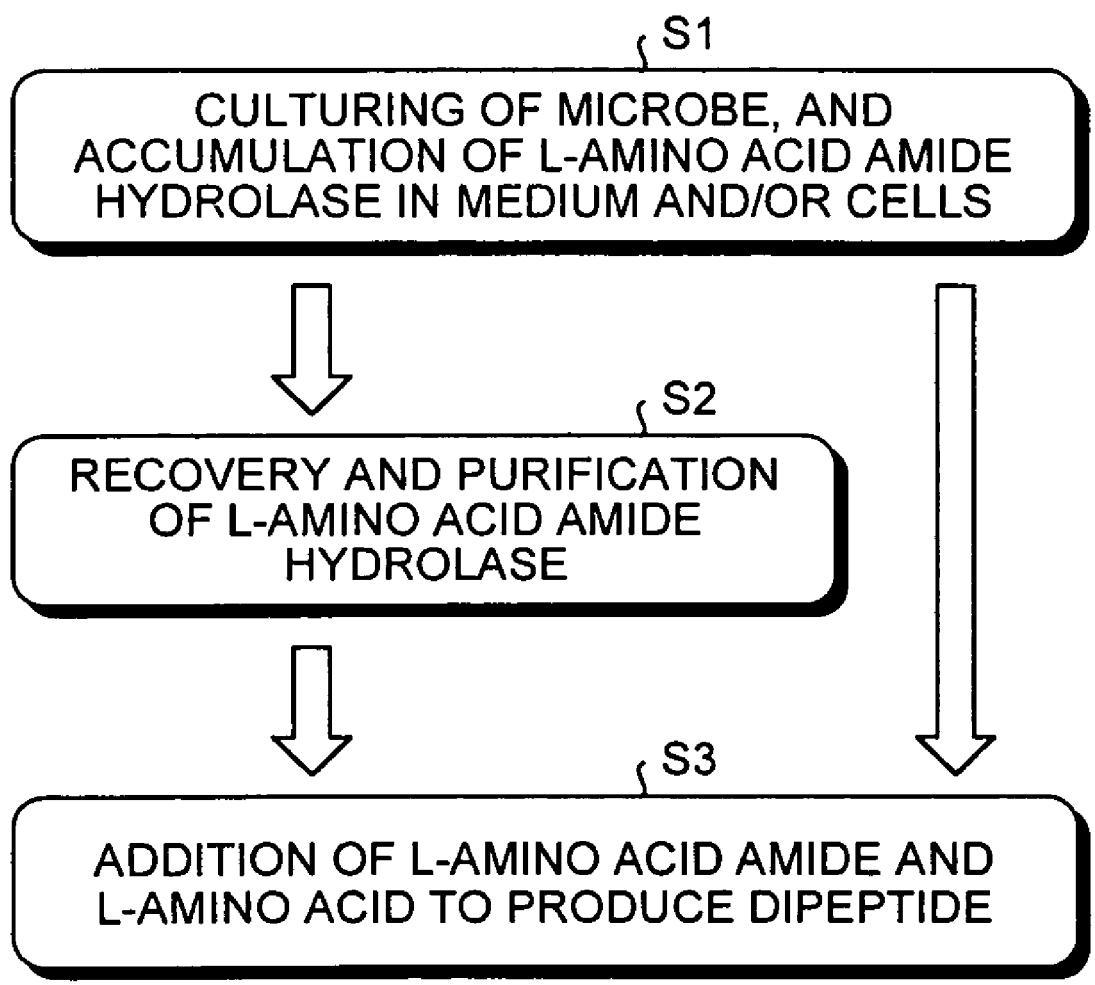
FIG. 1 is a flowchart of a dipeptide production method of the present invention.

The dipeptide production method of the present invention is characterized by using an enzyme or enzyme-containing substance having the ability to form a dipeptide from an L-amino acid amide and an L-amino acid, and more specifically, by using a culture of a microbe having the ability to form a dipeptide from an L-amino acid amide and an L-amino acid, microbial cells separated from the culture, or a treated microbial cell product from the microbe. The reaction in the dipeptide production method of the present invention is represented by the following reaction formula. As exemplified in the following chemical formula, the term "dipeptide" used in the present specification refers to a peptide polymer having one peptide bond.

The following provides an explanation of the dipeptide production method of the present invention with reference to the attached drawings presented in the order of:

[I] Microbes having the ability to form dipeptides from L-amino acid amides and L-amino acids;

[II] Properties of L-amino acid amide hydrolase;

[III] Isolation of a DNA that encodes a protein having an L-amino acid amide hydrolase activity; and,

[IV] A dipeptide production method.

[I] Microbes Having the Ability to form Dipeptides from L-Amino Acid Amides and L-Amino Acids Microbes having the ability to form dipeptides from L-amino acid amides and L-amino acids can be used without restriction for the microbe used in the present invention. Examples of microbes having the ability to form dipeptides from L-amino acid amides and L-amino acids include microbes belonging to the genus *Bacillus*, genus *Corynebacterium*, genus *Erwinia*, genus *Rhodococcus*, genus *Chryseobacterium*, genus *Micrococcus*, genus *Pseudomonas*, genus *Cryptococcus*, genus *Trichosporon*, genus *Rhodosporidium*, genus *Sporobolomyces*, genus *Tremela*, genus *Torulaspora*, genus *Sterigmatomyces* and genus *Rhodotorula*, and specific examples of these microbes are indicated below.

| | |
|---|---|
| *Bacillus megateirum* AJ3284 | FERM BP-8090 |
| *Corynebacterium glutamicum* | ATCC13286 |
| *Erwinia carotovora* AJ2719 | FERM BP-8089 |
| *Rhodococcus rhodochrous* | ATCC19149 |
| *Chryseobacterium meningosepticum* | ATCC13253 |
| *Micrococcus luteus* | ATCC9341 |
| *Pseudomonas saccharophila* | ATCC15946 |
| *Cryptococcus albidus* var. *albidus* | IFO0378 |
| *Trichosporon gracile* | ATCC24660 |
| *Rhodosporidium diobovatum* | ATCC22264 |
| *Sporobolomyces salmonicolor* | IFO1038 |
| *Tremela foliacea* | IFO9297 |
| *Torulaspora delbrueckii* | IFO1083 |
| *Sterigmatomyces elviae* | IFO1843 |
| *Rhodotorula ingeniosa* | ATCC22993 |

The depositary institutions of the aforementioned microbes are as indicated below.

The independent administrative corporation, International Patent Organism Depositary, National Institute for Advanced Industrial Science and Technology, Chuo Dai-6, 1-1 Higashi 1-Chome, Tsukuba-shi, Ibaraki-ken, Japan Institute for Fermentation, Osaka (IFO), 2-17-85 Jusanbon-cho, Yodogawa-ku, Osaka City, Japan American Type Culture Collection, P.O. Box 1549, Manassas, Va., USA Furthermore, *Bacillus megaterium* strain AJ3284 was deposited at the International Patent Organism Depositary of the independent administrative corporation, National Institute for Advanced Industrial Science and Technology on Jul. 13, 2001 and assigned the deposit number of FERM P-18421. Control of this organism was subsequently transferred to deposition based on the Budapest Treaty at the International Patent Organism Depositary of the independent administrative corporation, National Institute for Advanced Industrial Science and Technology on Jun. 25, 2002 and was assigned the deposit number of FERM BP-8090. In addition, *Erwinia carotovora* strain AJ2719 was deposited at the International Patent Organism Depositary of the independent administrative corporation, National Institute for Advanced Industrial Science and Technology on Jul. 13, 2001 and assigned the deposit number of FERM P-18420. Control of this organism was subsequently transferred to deposition based on the Budapest Treaty at the International Patent Organism Depositary of the independent administrative corporation, National Institute for Advanced Industrial Science and Technology, Chuo Dai-6, 1-1 Higashi 1-Chome, Tsukuba-shi, Ibaraki-ken, Japan on Jun. 25, 2002 and was assigned the deposit number of FERM BP-8089.

Wild strains or variant strains may be used for these microbes, and recombinant strains and so forth derived by cell fusion, genetic manipulation or other genetic techniques may also be used.

It is recommended that these microbes be cultured and grown in a suitable medium in order to obtain microbial cells of these microbes. There is no particular restriction on the medium used for this purpose so far as it allows the microbes to grow. The medium may be an ordinary medium that contains ordinary carbon sources, nitrogen sources, inorganic ions, and organic nutrient sources as necessary.

For example, any carbon source may be used so far as it can be utilized by the microbes. Specific examples of the carbon source that can be used include sugars such as glucose, fructose, maltose and amylose, alcohols such as sorbitol, ethanol and glycerol, organic acids such as fumaric acid, citric acid, acetic acid and propionic acid and their salts, hydrocarbons such as paraffin as well as mixtures thereof.

Examples of nitrogen sources that can be used include ammonium salts of inorganic acids such as ammonium sulfate and ammonium chloride, ammonium salts of organic salts such as ammonium fumarate and ammonium citrate, nitrates such as sodium nitrate and potassium nitrate, organic nitrogen compounds such as peptones, yeast extract, meat extract and corn steep liquor as well as mixtures thereof.

In addition, ordinary nutrient sources used in media, such as inorganic salts, trace metal salts and vitamins, can also be suitably mixed and used.

Microbial cells having a high level of activity to form dipeptides from L-amino acid amides and L-amino acids may be obtained in some cases by further adding an L-amino acid amide to the medium.

There is no particular restriction on culturing conditions, and culturing may be carried out, for example, for about 12 to about 48 hours while suitably controlling the pH and temperature to a pH range of 5 to 8 and a temperature range of 20 to 40° C., respectively, under aerobic conditions.

[II] Properties of L-Amino Acid Amide Hydrolase

An explanation is provided of the properties of an L-amino acid amide hydrolase purified for use as an enzyme having activity to form dipeptides from L-amino acid amides and L-amino acids taking *Corynebacterium glutamicum* strain ATCC 13286 of the aforementioned microbes as an example.

The L-amino acid amide hydrolase has activity to form an L-amino acid by hydrolyzing and L-amino acid amide, and activity to form a dipeptide by using an L-amino acid amide and an L-amino acid as substrates. When taking as an example the case of using L-alanine amide and L-glutamine as raw materials (substrates), the L-amino acid amide hydrolase at least has activity to form L-alanine by hydrolyzing L-alanine amide, and activity to form L-alanyl-L-glutamine by using L-alanine amide and L-glutamine as substrates. In addition, in taking as an example the case of using L-alanine amide and L-asparagine as raw materials, the L-amino acid amide hydrolase at least has activity to form L-alanine by hydrolyzing L-alanine amide, and activity to form L-alanyl-L-asparagine by using L-alanine amide and L-asparagine as substrates.

With respect to the enzyme function, when taking as an example the case of using L-alanine amide and L-glutamine or L-asparagine as raw materials, the L-amino acid amide hydrolase forms 1 molecule of L-alanine and 1 molecule of ammonia by hydrolyzing 1 molecule of L-alanine amide, forms 1 molecule of L-alanyl-L-glutamine and 1 molecule of ammonia from 1 molecule of L-alanine amide and 1 molecule of L-glutamine, and forms 1 molecule of L-alanyl-L-asparagine and 1 molecule of ammonia from 1 molecule of L-alanine amide and 1 molecule of L-asparagine.

The optimum pH is in the vicinity of 6.0 to 10.0, and the optimum temperature is in the vicinity of 30° C. to 50° C. The molecular weight of the subunit is calculated to be 42,000 to 46,000 as determined by SDS-polyacrylamide gel electrophoresis.

[III] Isolation of a DNA Encoding a Protein Having an L-Amino Acid Amide Hydrolase Activity The enzyme or enzyme-containing substance that catalyzes a reaction that produces dipeptides from L-amino acid amides and L-amino acids used in the present invention can be obtained by producing a transformant by isolating a DNA that encodes the enzyme using genetic engineering techniques from the aforementioned microbes having the enzyme.

For example, the following provides an explanation of a DNA encoding a protein having an L-amino acid amide hydrolase activity isolated from *Corynebacterium glutamicum* [III-1] along with a transformant in which it has been inserted [III-2].

[III-1] DNA Isolation

First, the amino acid sequence is determined for the purified L-amino acid amide hydrolase. The amino acid sequence can be determined using the Edman's method (see Edman, P., Acta Chem. Scand., 4, 227 (1950)). In addition, the amino acid sequence can also be determined using a sequencer manufactured by Applied Biosystems. The amino acid sequence is determined for the N-terminal or about 10 to about 30 residues of the peptide obtained by treatment with lysyl endopeptidase or the like for the purified L-amino acid amide hydrolase, and the base sequence of a DNA that encodes the hydrolase can be deduced based on the determined amino acid sequence. Universal codons are employed for deducing the base sequence of the DNA.

A DNA molecule of about 30 base pairs is synthesized based on the deduced base sequence. A method for synthesizing the DNA molecule is disclosed in Tetrahedron Letters, 22, 1859 (1981). In addition, the DNA molecule can also be synthesized using a synthesizer (manufactured by Applied Biosystems). DNA that encodes the L-amino acid amide hydrolase can then be amplified from a chromosomal DNA by a PCR method using the DNA molecule as a primer. However, since the DNA that has been amplified using the PCR method does not contain the full-length DNA that encodes the L-amino acid amide hydrolase, the full-length DNA that encodes the L-amino acid amide hydrolase is isolated from a gene library using the DNA that is amplified by use of the PCR method as a probe.

Alternatively, in the case where a portion of the base sequence of the gene is known, the full-length DNA that encodes a peptide-forming enzyme can be isolated from a chromosomal gene library using a DNA having the known sequence as a probe.

Moreover, in the case where the base sequence of the gene has homology with a known sequence, the full-length DNA that encodes the peptide-forming enzyme can be isolated from a chromosomal gene library using a DNA having that known sequence as a probe.

A procedure for the PCR method is described in White, T. J. et al., Trends Genet. 5, 185 (1989). A method for preparing a chromosomal DNA, as well as a method for isolating a target DNA molecule from a gene library using a DNA molecule as a probe, is described in Molecular Cloning, 2nd edition, Cold Spring Harbor Press (1989).

A method for determining the base sequence of an isolated DNA that encodes an L-amino acid amide hydrolase is described in A Practical Guide to Molecular Cloning, John Wiley & Sons, Inc. (1985). In addition, the base sequence can also be determined using a DNA sequencer (Applied Biosystems). A DNA that encodes the L-amino acid amide hydrolase isolated from *Corynebacterium glutamicum* strain ATCC 13286 in this manner is shown in SEQ ID No.: 4. The base sequence that consists of bases nos. 57 to 1295 out of the base sequence of SEQ ID No.: 4 is a CDS (coding region) (in the present specification, the "base sequence described in SEQ ID No.: 4" indicates a CDS portion unless otherwise indicated specifically). Furthermore, although the amino acid amide hydrolase described in SEQ ID No.: 4 is inherently the result of isolating a gene based on a purified enzyme using an alanine amide hydrolase activity as an indicator, it is referred to as amino acid amide hydrolase because its substrate specificity is not limited to alanine amide, but rather has an extremely broad spectrum.

A DNA that can be used in the present invention is not only the DNA specified in SEQ ID No.: 4. With respect to the DNA of SEQ ID No.: 4 isolated from *Corynebacterium glutamicum* strain ATCC 13286, even a DNA that has been artificially mutated to a DNA that encodes the L-amino acid amide hydrolase isolated from the chromosomal DNA of *Corynebacterium glutamicum* strain ATCC 13286 is also a DNA of the present invention so far as it encodes an L-amino acid amide hydrolase. A frequently used method for artificially mutating a DNA is the site-specific mutation introduction method described in Methods in Enzymol., 154 (1987).

In addition, a DNA having a base sequence that hybridizes with a polynucleotide having a base sequence complementary to the base sequence of base nos. 57 to 1295 described in SEQ ID No.: 4 under stringent conditions, and encodes a protein having an L-amino acid amide hydrolase activity, can also used as a DNA in the present invention. The "stringent conditions" mentioned herein refer to conditions under which a so-called specific hybrid is formed while non-specific hybrids are not formed. Although it is difficult to clearly quantify these conditions, examples of such conditions include conditions under which DNAs having high degrees of homology, such as DNAs having a homology of 50% or more, preferably 80% or more, and more preferably 90% or more, hybridize with each other while DNAs having low degrees of homology do not hybridize with each other, and conditions under which DNAs hybridize at a salt concentration equivalent to 60° C., 1×SSC and 0.1% SDS, preferably 60° C., 0.1×SCC and 0.1% SDS, and more preferably 65° C., 0.1×SSC and 0.1% SDS, which are the conditions for washing of ordinary Southern hybridization. The activity of L-amino acid amide hydrolase is as previously described. However, in the case of a base sequence that hybridizes under stringent conditions with a base sequence complementary to the base sequence of bases nos. 57 to 1295 described in SEQ ID No.: 4 of the Sequence Listing, it preferably retains about 10%, and preferably about 50% or more, of the enzyme activity of a protein having the amino acid sequence described in SEQ ID No.: 5 of the Sequence Listing under conditions of 50° C. and pH 8.

Moreover, a protein substantially identical to the L-amino acid amide hydrolase encoded by the DNA described in SEQ ID No.: 4 of the Sequence Listing can also be used in the present invention. Thus, a DNA that encodes a "protein having an amino acid sequence containing a substitution, deletion, insertion, addition or inversion of one or a plurality of amino acids in the amino acid sequence described in SEQ ID No.: 5 of the Sequence Listing, and having the activity of an L-amino acid amide hydrolase that forms a dipeptide from an L-amino acid amide and an L-amino acid" can also be used in the present invention. Here, the term "a plurality of" refers to a range that does not significantly impair the three-dimensional structure of the protein of the amino acid residues or the activity of L-amino acid amide hydrolase, and more specifically is a value of 2 to 50, preferably a value of 2 to 30, and more preferably a value of 2 to 10. In addition, the activity of the L-amino acid amide hydrolase is as previously explained. However, in the case of an amino acid sequence containing a substitution, deletion, insertion, addition or inversion of one or a plurality of amino acid residues in the amino acid sequence described in SEQ ID No.: 5 of the Sequence Listing, it preferably retains about 10%, and preferably about 50% or more, of the enzyme activity of a protein having the amino acid sequence described in SEQ ID No.: 5 of the Sequence Listing under conditions of 50° C. and pH 8.

As has been described above, in the case of having isolated a DNA derived from, for example, *Corynebacterium glutamicum* strain ATCC 13286, the following DNA can be preferably used in the present invention:

(i) A DNA composed of the base sequence of bases nos. 57 to 1295 described in SEQ ID No.: 4 of the Sequence Listing;

(ii) A DNA that hybridizes under stringent conditions with a polynucleotide that consists of a base sequence complementary to the base sequence of bases nos. 57 to 1295 described in SEQ ID No.: 4 of the Sequence Listing, and encodes protein having an L-amino acid amide hydrolase activity that catalyzes a reaction that produces a dipeptide from an L-amino acid amide and an L-amino acid;

(iii) A DNA that encodes a protein having the amino acid sequence described in SEQ ID No.: 5 of the Sequence Listing; and, (iv) A DNA that encodes a protein having an amino acid sequence that contains a substitution, deletion, insertion, addition or inversion of one or a plurality of amino acids in the amino acid sequence described in SEQ ID No.: 5 of the Sequence Listing, and having an L-amino acid amide hydrolase activity that catalyzes a reaction that produces a dipeptide from an L-amino acid amide and an L-amino acid.

[III-2] Production of Transformant

Next, production of a transformant that expresses a protein having an L-amino acid amide hydrolase activity will be explained. Numerous examples are known of producing enzymes, physiologically active substances and other useful proteins by using recombinant DNA technology, and the use of recombinant DNA technology allows mass production of useful proteins that naturally occur only in trace amounts.

Preferable examples of a transformant that can be used in the method of the present invention include the transformants capable of expressing the protein (A), (B) or (C) below:

(A) A protein having the amino acid sequence described in SEQ ID No.: 5 of the Sequence Listing, (B) A protein having an amino acid sequence that contains a substitution, deletion, insertion, addition or inversion of one or a plurality of amino acids in the amino acid sequence described in SEQ ID No.: 5 of the Sequence Listing, and having an L-amino acid amide hydrolase activity that catalyzes a reaction that produces a dipeptide from an L-amino acid amide and an L-amino acid, (C) A protein encoded by a DNA that hybridizes under stringent conditions with a polynucleotide composed of a base sequence complementary to the base sequence of SEQ ID No.: 4 of the Sequence Listing, and encodes a protein having an L-amino acid amide hydrolase activity that catalyzes a reaction that produces a dipeptide from an L-amino acid amide and an L-amino acid.

To produce a transformant that expresses a protein of the aforementioned (A) to (C) having an L-amino acid amide hydrolase activity, it suffices that the DNA of (i) to (iv) indicated in the aforementioned section [III-1] should be inserted into host cells. Namely, the DNA of (i), (ii), (iii) or (iv) is incorporated into an expression vector capable of expressing in the host cells followed by introduction of the expression vector into host cells.

In the case of mass-production of a protein using recombinant DNA technology, conjugating the protein within a transformant that produces the protein to form an inclusion body of protein is also a preferable mode for carrying out the present invention. Advantages of this expression and production method include protection of the target protein from digestion by proteases present within microbial cells, and simple purification of the target protein by crushing of the microbial cells followed by centrifugal separation.

The protein inclusion bodies obtained in this manner are converted to a properly folded, physiologically active protein after going through an activity regeneration procedure consisting primarily of solubilizing the protein with a protein denaturant followed by removal of the denaturant. There are numerous examples of this, including regeneration of the activity of human interleukin-2 (Japanese Patent Application Laid-open Publication No. S61-257931).

In order to obtain an active protein from the inclusion bodies of protein, a series of operations including solubilization and activity regeneration are required, and the procedure is more complex than in the case of producing the active protein directly. However, in the case of mass-producing a protein that has a detrimental effect on microbial growth within microbial cells, that effect can be suppressed by accumulating the protein in the form of inactive inclusion bodies of protein within the microbial cells.

Examples of methods for mass-producing a target protein in the form of inclusion bodies include a method in which a target protein is expressed independently under the control of a powerful promoter, and a method in which a target protein is expressed in the form of a fused protein fused with a protein that is known to be expressed in large amounts.

Moreover, it is also effective to arrange the recognition sequence of a restricting protease at a suitable location in order to cut out the target protein following expression in the form of a fused protein.

In the case of mass-production of a protein using recombinant DNA technology, although examples of host cells that are transformed include bacterial cells, *Actinomyces* cells, yeast cells, mold cells, plant cells and animal cells, intestinal bacteria such as *Escherichia coli* are commonly used, with *Escherichia coli* being used preferably. This is because there are numerous pieces of information that are available regarding techniques for mass-production of a protein using *Escherichia coli*. The following provides an explanation of one mode of a method for producing an L-amino acid amide hydrolase using transformed *Escherichia coli*.

Promoters normally used in heterogeneous protein production in *Escherichia coli* can be used as a promoter for expressing a DNA encoding an L-amino acid amide hydrolase. Examples of the promoters include powerful promoters such as T7 promoter, trp promoter, lac promoter, trc promoter, tac promoter, lambda phage $P_R$ promoter and $P_L$ promoter.

To produce an L-amino acid amide hydrolase in the form of an inclusion body of fused protein, a gene that encodes another protein, and preferably a hydrophilic peptide, may be ligated upstream or downstream of the L-amino acid amide hydrolase gene to obtain a fused protein gene. Such a gene that encodes another protein may be one that provides an increased accumulation amount of the fused protein and an enhanced solubility of the fused protein after the denaturation and regeneration steps. Candidates for such a gene include, for example, T7 gene 10, β-galactosidase gene, dehydrofolate reductase gene, interferon γ gene, interleukin-2 gene and prochymosin gene.

When ligating these genes to a gene that encodes an L-amino acid amide hydrolase, the codon reading frames are made to match. They may either be ligated at a suitable restrictase site or a synthetic DNA of a suitable sequence may be used.

In addition, in order to increase the amount of production, it may be preferable to ligate a transcription terminating sequence in the form of a terminator downstream of the fused protein gene. Examples of this terminator include T7 terminator, fd phage terminator, T4 terminator, tetracycline resistance gene terminator and *Escherichia coli* trpA gene terminator.

So-called multi-copy vectors are preferable as the vector for introducing into *Escherichia coli* a gene that encodes an L-amino acid amide hydrolase or a fused protein consisting of an L-amino acid amide hydrolase and another protein, examples of which include plasmids having a replication starting point originating in ColE1 such as pUC plasmid, pBR322 plasmid or derivatives thereof. A "derivative" refers to the result of modifying the plasmid by base substitution, deletion, insertion, addition or inversion. Furthermore, the modification referred to here includes modification resulting from mutagenesis treatment by a mutagen or UV irradiation, or spontaneous mutation. More specifically, examples of vectors that can be used include pUC19, pUC18, pBR322, pHSG299, pHSG298, pHSG399, pHSG398, RSF1010, pMW119, pMW118, pMW219 and pMW218. Further, vectors of phage DNA can also be used.

In addition, the vector preferably has a marker such as an ampicillin resistant gene in order to screen out the transformant. Expression vectors having powerful promoters are commercially available for use as such plasmids (such as pUC vector (manufactured by Takara Shuzo), pPROK vector (manufactured by Clontech) and pKK233-2 vector (manufactured by Clontech).

A recombinant DNA is obtained by ligating a DNA fragment to a vector DNA. In this case, a promoter, a gene encoding L-amino acid amide hydrolase or a fused protein consisting of an L-amino acid amide hydrolase and another protein, and depending on the case, a terminator are ligated in that order.

Transformation of *Escherichia coli* using the recombinant DNA and culturing the resulting *Escherichia coli* results in expression and production of an L-amino acid amide hydrolase or a fused protein consisting of an L-amino acid amide hydrolase and another-protein. Although a strain that is normally used in the expression of a heterogeneous gene can be used as a host to be transformed, *Escherichia coli* strain JM109, for example, is preferable. Methods for carrying out transformation and methods for screening out transformants are described in Molecular Cloning, 2nd Edition, Cold Spring Harbor Press (1989) and other publications.

When expressed as a fused protein, the L-amino acid amide hydrolase may be cut out with a restriction protease that uses a sequence not present in the L-amino acid amide hydrolase, such as blood coagulation factor Xa or kallikrein, as a recognition sequence.

A medium normally used for culturing *Escherichia coli*, such as M9-casamino acid medium or LB medium, may be used for the production medium. In addition, culturing conditions and production induction conditions are suitably selected depending on the marker of the vector used, promoter, type of host microbe and so forth.

The following method can be used to recover the L-amino acid amide hydrolase or fused protein consisting of an L-amino acid amide hydrolase and another protein. If the L-amino acid amide hydrolase or its fused protein has been solubilized within the microbial cells, after the recovery of the microbial cells, the microbial cells are crushed or lysed so that they can be used as a crude enzyme liquid. Moreover, the L-amino acid amide hydrolase or its fused protein can be purified prior to use by ordinary techniques such as precipitation or filtration, column chromatography as necessary. In this case, a purification method can also be used that uses antibody of the L-amino acid amide hydrolase or its fused protein.

In the case where inclusion bodies of protein are formed, the inclusion bodies are solubilized with a denaturant. Although they may be solubilized with the microbial cell protein, in consideration of the following purification procedure, the inclusion bodies are preferably taken out and then solubilized. Known methods may be used to recover the inclusion bodies from the microbial cells. For example, inclusion bodies can be recovered by crushing the microbial cells followed by centrifugal separation. Examples of denaturants capable of solubilizing inclusion bodies of protein include guanidine hydrochloride (for example, 6 molars (M), pH 5 to 8) and urea (for example, 8 M).

Protein having activity is regenerated by removing these denaturants by dialysis, for example. Tris-HCl buffer solution or phosphate buffer solution and so forth may be used as the dialysis solution used in dialysis, and the concentration, may be, for example, 20 millimolars (mM) to 0.5 M, while the pH may be, for example, 5 to 8.

The protein concentration during the regeneration step is preferably held to about 500 μg/ml or less. The dialysis temperature is preferably equal to or lower than 5° C. to inhibit the occurrence of self-crosslinking by the regenerated L-amino acid amide hydrolase. Moreover, in addition to dialysis, dilution or ultrafiltration may be used to remove the denaturants, and regeneration of the enzyme activity can be expected by employing any one of these method.

In the case of using the DNA indicated in SEQ ID No.: 4 of the Sequence Listing for the DNA that encodes an L-amino acid amide hydrolase, the L-amino acid amide hydrolase that has the amino acid sequence described in SEQ ID No.: 5 is produced.

It should be noted that genetic engineering techniques can be carried out in accordance with the techniques described in the literature such as Molecular Cloning, 2nd edition, Cold Spring Harbor Press (1989).

[IV] Dipeptide Production Method

The dipeptide production method of the present invention produces a dipeptide from an L-amino acid amide and an L-amino acid using an enzyme or enzyme-containing substance having the ability to form a dipeptide from an L-amino acid amide and an L-amino acid, and more specifically, a culture of microbes, microbial cells separated from the culture or treated microbial cells from the microbe.

The aforementioned L-amino acid amide hydrolase has activity that forms an L-amino acid by hydrolyzing L-amino acid amide, and activity that produces a dipeptide by using an L-amino acid amide and an L-amino acid as substrates.

FIG. 1 is a flowchart of the dipeptide production method of the present invention.

First, microbes having the ability to form a dipeptide from an L-amino acid amide and an L-amino acid are cultured in a medium, and an L-amino acid amide hydrolase is produced and accumulated in the culture and/or cells (Step S1).

Next, a purified L-amino acid amide hydrolase is produced by recovering and purifying the L-amino acid amide hydrolase (Step S2).

Subsequently, a dipeptide can be produced in large amounts by adding the L-amino acid amide and the L-amino acid to the purified L-amino acid amide hydrolase produced in Step S2 or the L-amino acid amide hydrolase accumulated in Step S1, and allowing reaction to proceed (Step S3).

For the method by which the L-amino acid amide hydrolase produced by the aforementioned microbes is allowed to act on the L-amino acid amide and the L-amino acid, the substrates may be added either directly to the culture liquid while culturing the aforementioned microbes, or microbial cells may be separated from the microbial culture by centrifugation and so forth, followed by resuspending them in buffer either directly or after washing, and then adding L-amino acid amide and L-amino acid followed by allowing the resultant to react. Alternatively, microbial cells can be used that have been immobilized by known methods using polyacrylamide gel, carrageenan, alginic acid gel and the like.

In addition, crushed microbial cells, acetone-treated microbial cells or freeze-dried microbial cells may be used as the treated microbial cell product. Methods such as ultrasonic crushing, French press crushing and glass bead crushing are used for crushing microbial cells, while methods using egg white lysozyme, peptidase treatment or a suitable combination thereof are used in the case of lysing microbial cells.

Moreover, L-amino acid amide hydrolase may be recovered from the treated microbial cell product and used as a crude enzyme liquid, or the enzyme may be purified before use as necessary. Ordinary enzyme purification methods can be used for purifying the enzyme obtained from a culture. More specifically, microbial cells are collected by centrifugal separation and so forth, the cells are then crushed by mechanical methods such as ultrasound treatment, glass beads or a dynomill, and solid materials such as cell fragments are removed by centrifugal separation to obtain crude enzyme followed by purification of the aforementioned L-alanine amide hydrolase by performing ultracentrifugation fractionation, salting out, organic solvent precipitation, ion exchange chromatography, adsorption chromatography, gel filtration chromatography, hydrophobic chromatography and so forth.

Namely, in the case of a fraction having activity to form a dipeptide from an L-amino acid amide and an L-amino acid, the entire enzyme and enzyme-containing substance can be used. Here, an "enzyme-containing substance" refers to any substance that contains the enzyme, and includes specific forms such as a culture of microbes that produce the enzyme, microbial cells separated from the culture and treated microbial cells. A culture of microbes refers to a thing that is obtained by culturing microbes, and more specifically, refers to a mixture of microbial cells, the medium used to culture the microbes and substances produced by the cultured microbes. In addition, the microbial cells may be washed and used as washed microbial cells, or immobilized cells may be used that have been immobilized by covalent bonding, adsorption or inclusion methods. In addition, since some microbes are partially lysed during culturing depending on the microbes used, the culture supernatant may also be used as the enzyme-containing substance in such cases.

The amount of enzyme or enzyme-containing substance used should be an amount at which the target effect is demonstrated (hereinafter, "effective amount"), and although this effective amount can be easily determined through simple, preliminary experiment by a person with ordinary skill in the art, in the case of using washed cells, for example, the amount used is 1 to 500 grams (g) per liter of the reaction mixture.

Any L-amino acid amide can be used for the L-amino acid amide so far as it is an L-amino acid amide that can be hydrolyzed at the substrate specificity of the L-amino acid amide hydrolase. Examples of the L-amino acid amide include not only L-amino acid amides corresponding to naturally-occurring amino acids, but also L-amino acid amides corresponding to non-naturally-occurring amino acids or their derivatives. In addition, since the L-amino acid amide hydrolase used in the present invention imparts L-amino acid amide by asymmetrically hydrolyzing a racemic L-amino acid amide, racemic amino acid amides that can be inexpensively synthesized with the Strecker method can also be used. In the present invention, preferable examples of L-amino acid amides include L-alanine amide, glycine amide and L-aspartic acid amide, with L-alanine amide being particularly preferable.

There is no particular restriction on the L-amino acid so far as it can form a dipeptide with an L-amino acid amide at a substrate specificity of the L-amino acid amide hydrolase, and known L-amino acids can be used. Preferable examples of L-amino acids include L-glutamine, L-asparagine, glycine, L-alanine, L-valine, L-leucine, L-isoleucine, L-methionine, L-proline, L-phenylalanine, L-tryptophan, L-serine, L-threonine, L-tyrosine, L-lysine, L-arginine, L-histidine and L-glutamine, with L-glutamic acid and L-asparagine being particularly preferable.

Dipeptides may be produced by selecting one type each of the aforementioned L-amino acid amide and L-amino acid, or dipeptides may be produced by selecting two or more types.

Concentrations of the L-amino acid amide and L-amino acid used as starting materials are each 1 mM to 10 M, and preferably 0.1 M to 2 M. However, in some cases, it is preferable to add an amount of L-amino acid equal to or greater than the amount of L-amino acid amide. In addition, when needed, for example, in the case where high concentrations of substrates inhibit the reaction, these can be successively added during the reaction after adjusting them to concentrations that do not result in inhibition.

The reaction temperature is 10 to 70° C., and preferably 20 to 50° C., while the reaction pH is 2 to 12, and preferably 3 to 11. By carrying out the reaction in this manner for about 2 to 48 hours, dipeptide is produced and accumulates in the reaction mixture. Since the dipeptide production reaction is an equilibrium reaction, in order to achieve efficient production, the reaction is allowed to proceed further by separating the dipeptide and ammonia produced.

EXAMPLES

Hereinafter, the present invention will be explained in more detail by way of examples. However, the present invention should not be considered to be limited to these examples. Note that in the examples, quantitative determination of L-alanine, L-alanyl-L-glutamine or L-alanyl-L-asparagine was carried out by a method using high-performance liquid chromatography (column: Inertsil ODS-2 manufactured by GL Science, eluate: aqueous phosphate solution (pH 2.1), 2.5 mM sodium 1-octanesulfonate/methanol=10/1, flow rate: 1.0 mL/min, detection: 210 nanometers (nm)).

Example 1

Production of L-Alanyl-L-Asparagine

A 50 milliliter (ml or mL) aliquot of a medium containing 0.5% (w/v) yeast extract, 0.5% (w/v) peptone, 0.5% (w/v) glycerol, 0.5% (w/v) sodium chloride and 0.5% (w/v) L-alanine amide hydrochloride (pH 7.0) was dispensed to a 500 mL Sakaguchi flask and sterilized at 120° C. for 20 minutes. One loopful of the microbes shown in Table 1, which were cultured at 30° C. for 24 hours on a slant medium containing 0.5% (w/v) yeast extract, 0.5% (w/v) peptone, 0.5% (w/v) glycerol, 0.5% (w/v) sodium chloride, 0.5% (w/v) L-alanine amide hydrochloride and 2% (w/v) agar (pH 7.0), was inoculated into the aforementioned medium and cultured by shake culturing for 20 hours at 30° C. and 120 strokes/minute. Following the culturing, the microbial cells were separated by centrifugation, washed twice with an amount of physiological saline equal to the amount of culture liquid and centrifuged again to collect the microbial cells followed by suspending with 0.2 M Tris-HCl buffer (pH 9.0) to a final volume of 10 mL. 1 mL of this microbial cell suspension was then added to 4 mL of the aforementioned buffer containing 62.5 mM L-alanine amide hydrochloride and 250 mM L-asparagine, and after bringing to a total volume of 5 mL, was allowed to react at 30° C. for 24 hours. A lot in which microbial cells were not added was established as a control experiment. The results are shown in Table 1.

TABLE 1

| Microbe | L-Ala-L-Asn produced (mM) |
|---|---|
| *Bacillus megateirum* FERM BP-8090 | 0.4 |
| *Corynebacterium glutamicum* ATCC13286 | 1.8 |
| *Erwinia carotovora* FERM BP-8089 | 0.5 |
| *Rhodococcus rhodochrous* ATTC19149 | 1.0 |
| *Chryseobacterium meningosepticum* ATTC13253 | 0.1 |
| *Micrococcus luteus* ATCC9341 | 0.1 |
| *Pseudomonas saccharophila* ATCC9114 | 0.1 |
| *Cryptococcus albidus* IFO610 | 1.8 |
| *Trichosporon gracile* ATCC24660 | 2.5 |
| *Rhodosporidium diobovatum* ATCC22264 | 2.7 |
| *Sporobolomyces salmonicolor* IFO1038 | 1.5 |
| *Tremela foliacea* IFO9297 | 3.3 |
| *Torulaspora delbrueckii* IFO1083 | 2.9 |
| *Sterigmatomyces elviae* IFO1843 | 0.1 |
| *Rhodotorula ingeniosa* ATCC22993 | 0.1 |
| Microbial cells not added | Below detection limit |

L-Ala-L-Asn: L-alanyl-asparagine

Example 2

Purification of L-Alanine Amide Hydrolase from *Cotynebacterium glutamicum* Strain ATCC 13286

Measurement of enzyme titer was carried out in the manner described below. 200 micromoles (μmol) of Tris-HCl buffer (pH 9.0), 50 μmol of L-alanine amide hydrochloride and a suitable amount of enzyme liquid were added and mixed to bring to a final volume of 1 ml, and allowed to react at 30° C. for 60 minutes. Then, 4 ml of aqueous phosphate solution (pH 2.1) was added to stop the reaction. The L-alanine produced was quantified by high-performance liquid chromatography. The amount of enzyme that produced 1 μmol of L-alanine in 1 minute was defined as 1 unit of enzyme.

8 liters (L) of *Corynebacterium glutamicum* strain ATCC 13286 was cultured in the same manner as Example 1 followed by collection of the microbial cells by centrifugal separation. The following procedure was carried out on ice or at 4° C. After washing the microbial cells with 50 mM potassium phosphate buffer (pH 7.0), the cells were subjected to crushing treatment for about 10 minutes using glass beads having a diameter of 0.1 mm. The glass beads and crushed cell liquid were then separated, and the crushed cell fragments were removed by centrifugal separation for 30 minutes at 20,000×g to obtain a cell-free extract. Moreover, the insoluble fraction was removed by ultracentrifugation for 60 minutes at 200,000×g to obtain a soluble fraction in the form of the supernatant. Ammonium sulfate was then added to the resulting soluble fraction to 60% saturation followed by recovery of the precipitate by centrifuging for 30 minutes at 20,000×g. The resulting precipitate was dissolved in a small amount of 50 mM potassium phosphate buffer (pH 7.0) and then dialyzed against 50 mM potassium phosphate buffer (pH 7.0). This enzyme liquid was then applied to a Q-Sepharose HP column pre-equilibrated with 50 mM potassium phosphate buffer (pH 7.0), and the enzyme was eluted over a linear concentration gradient of 50 mM potassium phosphate buffer (pH 7.0) containing 0 to 1.0 M sodium chloride. The active fraction was collected and applied to a Superdex 200 pg column pre-equilibrated with 50 mM potassium phosphate buffer (pH 7.0), and the enzyme was then eluted with the same buffer. The active fraction was collected and dialyzed against 20 mM potassium phosphate buffer (pH 7.0) containing 0.5 M ammonium sulfate, and then applied to a Phenyl-Sepharose HP column pre-equilibrated with 20 mM potassium phosphate buffer (pH 7.0) containing 0.5 M ammonium sulfate. The enzyme was then eluted over a linear concentration gradient of 20 mM potassium phosphate buffer (pH 7.0) containing 0.5 to 0 M ammonium sulfate. The active fraction was collected and dialyzed against 50 mM potassium phosphate buffer (pH 7.0), and this was then applied to a MonoQ column pre-equilibrated with 50 mM potassium phosphate buffer (pH 7.0), enzyme was eluted over a linear concentration gradient of 50 mM potassium phosphate buffer (pH 7.0) containing 0 to 1.0 M sodium chloride. L-alanine amide hydrolase was uniformly purified on the basis of electrophoresis in this manner. The total amounts of protein and specific activities in each purification step are shown in Table 2.

TABLE 2

| Step | Total activity (unit) | Total protein (mg) | Specific activity (unit/mg) |
|---|---|---|---|
| Cell-free extract | 80 | 2000 | 0.040 |
| Soluble fraction | 71 | 1690 | 0.042 |
| Ammonium sulfate fraction | 79 | 1080 | 0.073 |
| Q-Sepharose HP | 56 | 379 | 0.149 |
| Superdex200 pg | 21 | 151 | 0.135 |
| Phenyl-Sepharose HP | 12.5 | 6.60 | 1.897 |
| MonoQ | 2.4 | 0.24 | 9.841 |

Example 3

Evaluation of Molecular Weight of L-Alanine Hydrolase

The equivalent of 0.5 microgram (μg) of the purified enzyme preparation obtained according to the method of Example 2 was applied to polyacrylamide electrophoresis. 0.3% (w/v) Tris, 1.44% (w/v) glycine and 0.1% (w/v) sodium lauryl sulfate were used for the electrophoresis buffer, concentration gradient gel having a gel concentration of 10 to 20% (Multigel 10 to 20, manufactured by Daiichi Pure Chemicals) was used for the polyacrylamide gel, and precision pre-stained standards (manufactured by Biorad) were used for the molecular weight markers. Following completion of electrophoresis, the gel was stained with Coomassie brilliant blue R-250, and a uniform band was detected at the location calculated to have a molecular weight of 42,000 to 46,000.

Example 4

Evaluation of Optimum pH of L-Alanine Amide Hydrolase

Figure 2:
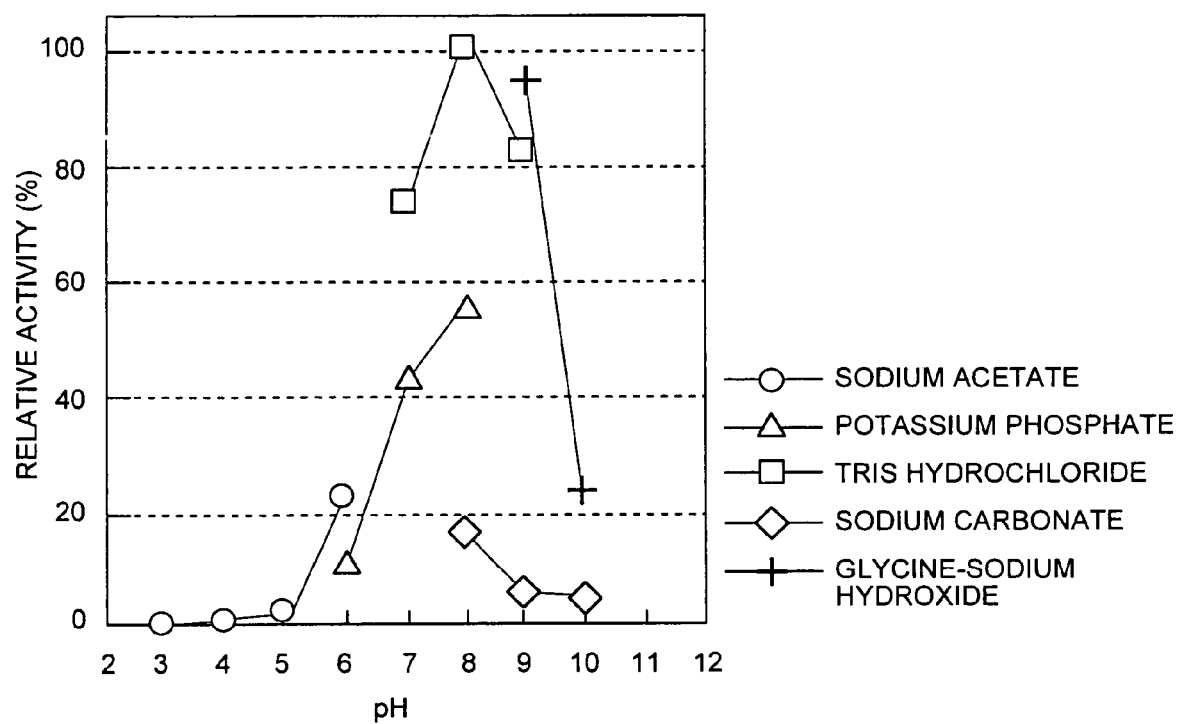
FIG. 2 is a graph of the optimum pH curve of an L-amino acid amide hydrolase derived from *Corynebacterium glutamicum* ATCC 13286.

L-alanine amide was hydrolyzed using the L-alanine amide hydrolase uniformly purified in Example 2 followed by evaluation of the pH for the reaction that produces L-alanine in the manner described below. 200 µmol of buffer solution consisting of sodium acetate buffer (pH 3.0 to 6.0), potassium phosphate buffer (pH 6.0 to 8.0), Tris-HCl buffer (pH 7.0 to 9.0), sodium carbonate buffer (pH 8.0 to 10.0) or glycine-sodium hydroxide buffer, 50 µmol of L-alanine amide hydrochloride and a suitable amount of enzyme liquid were added and mixed to a final volume of 1 ml followed by allowing to react at 30° C. for 60 minutes and evaluating enzyme activity. Those results when assigning a value of 100% to activity in the case of using Tris-HCl buffer (pH 8.0) are shown in FIG. 2.

Example 5

Evaluation of L-Alanine Amide Hydrolase Reaction Temperature

L-alanine amide was hydrolyzed using the L-alanine amide hydrolase uniformly purified in Example 2, followed by evaluation of the reaction temperature for the reaction that produces L-alanine in the manner described below. 200 µmol of Tris-HCl buffer, 50 µmol of L-alanine amide hydrochloride and a suitable amount of enzyme were added and mixed to a final volume of 1 ml, and then allowed to react at a temperature of 25, 30, 40, 50 or 60° C. for 60 minutes followed by evaluation of enzyme activity. Those results when assigning a value of 100% to activity in the case of a reaction temperature of 40° C. are shown in FIG. 3.

Example 6

Production of L-Alanyl-L-Asparagine and L-Alanyl-L-Glutamine

The L-alanine amide hydrolase uniformly purified in Example 2 was allowed to act on L-alanine amide hydrochloride and L-asparagine or L-alanine amide hydrochloride and L-glutamine to produce L-alanyl-L-asparagine or L-alanyl-L-glutamine. In the case of obtaining L-alanyl-L-asparagine, 200 µmol of Tris-HCl buffer (pH 9.0), 50 µmol or L-alanine amide hydrochloride, 150 µmol of L-asparagine and enzyme liquid containing 0.08 unit of L-alanine amide hydrolase were added and mixed to a final volume of 1 ml. In the case of obtaining L-alanyl-L-glutamine, the reactants were mixed under the same conditions as in the case of L-alanyl-L-asparagine with the exception of using 150 µmol of L-glutamine instead of 150 µmol of L-asparagine. Control experiments were established for the case of using one of the substrates or setting the lot in which enzyme was not added. The reaction was carried out at a reaction temperature of 30° C. for 10 hours, and the results of quantifying the target product are shown in Table 3.

TABLE 3

| Substrate | | Enzyme addition | Product | Product concentration (mM) |
|---|---|---|---|---|
| L-alanine amide | L-asparagine | Yes | L-alanyl-L-asparagine | 8.4 |
| L-alanine amide | — | Yes | L-alanyl-L-asparagine | Below detection limit |
| — | L-asparagine | Yes | L-alanyl-L-asparagine | Below detection limit |
| L-alanine amide | L-asparagine | No | L-alanyl-L-asparagine | Below detection limit |
| L-alanine amide | L-glutamine | Yes | L-alanyl-L-glutamine | 7.7 |
| L-alanine amide | — | Yes | L-alanyl-L-glutamine | Below detection limit |
| — | L-glutamine | Yes | L-alanyl-L-glutamine | Below detection limit |
| L-alanine amide | L-glutamine | No | L-alanyl-L-glutamine | Below detection limit |

Example 7

Isolation of L-Alanine Amide Hydrolase Gene

Hereinafter, isolation of L-alanine amide hydrolase gene and expression of L-alanine amide hydrolase in *Escherichia coli* (*E. coli*), will be described. *Corynebacterium glutamicum* strain ATCC 13286 was used for the microbe strain. *E. coli* JM109 was used for the host and pUC18 was used for the vector for both gene isolation and expression of L-alanine amide hydrolase.

1. Production of PCR Primer Based on Determined Amino Acid Sequence

Mixed primers having the base sequence indicated in SEQ ID No.: 2 and SEQ ID No.: 3, respectively, were produced based on N-terminal amino acid sequence of L-alanine amide hydrolase originating in the aforementioned *Corynebacterium glutamicum* strain ATCC 13286.

2. Acquisition of Microbial Cells

*Corynebacterium glutamicum* strain ATCC 13286 was cultured on CM2Gly agar medium (0.5 g/dl glycerol, 1.0 g/dl yeast extract, 1.0 g/dl peptone, 0.5 g/dl NaCl, 2 g/dl agar, pH 7.0) at 30° C. for 24 hours to refresh the microbe. One loopful thereof was then inoculated in a 500 ml-volume Sakaguchi flask containing 50 ml of CM2Gly liquid medium, followed by shake culturing at 30° C. for 16 hours under aerobic conditions.

3. Acquisition of Chromosomal DNA from Microbial Cells 50 ml of culture liquid were centrifuged (12,000 rounds per minute (rpm), 4° C., 15 minutes) to collect the microbial cells. These microbial cells were then suspended in 10 ml of 50 mM Tris-HCl buffer (pH 8.0) containing 20 mM EDTA followed by recovery of the microbial cells by centrifugal separation. The microbial cells were again suspended in 10 ml of 50 mM Tris-HCl buffer (pH 8.0) containing 20 mM EDTA. Moreover, after adding 0.5 ml of 20 mg/ml lysozyme solution and 1 ml of 10% SDS (sodium dodecyl sulfate) solution to this suspension, the solution was incubated at 55° C. for 20 minutes. The incubated solution was then deproteinized by the addition of an equal volume of phenol saturated with 10 mM Tris-HCl buffer (pH 8.0) containing 1 mM EDTA. An equal volume of 2-propanol was added to the separated aqueous layer to precipitate a DNA followed by recovery of that precipitated DNA. After dissolving the DNA precipitated in 0.5 ml of 50 mM Tris-HCl buffer (pH 8.0) containing 20 mM EDTA, 5 microliters (μl) of 10 mg/ml RNase and 5 μl of 10 mg/ml Proteinase K were added and allowed to react at 55° C. for 2 hours. After the reaction, this solution was deproteinized by the addition of an equal volume of phenol saturated with 10 mM Tris-HCl buffer (pH 8.0) containing 1 mM EDTA. Moreover, an equal volume of 24:1 chloroform/isoamyl alcohol was added to the separated aqueous layer to recover the aqueous layer. To the aqueous layer obtained by doing the procedure two times, 3 M sodium acetate solution (pH 5.2) was added to bring to a final concentration of 0.4 M and 2 volumes of ethanol was added. The DNA that was formed as a precipitate was recovered, and after washing with 70% ethanol, was dried and dissolved in 1 ml of 10 mM Tris-HCl buffer (pH 8.0) containing 1 mM EDTA.

4. Acquisition of DNA Fragment Containing a Portion of L-Alanine Amide Hydrolase Gene by Cassette PCR Method The TaKaRa LA PCR In Vitro Cloning Kit (Takara Shuzo) was used for isolation and amplification of DNA molecules containing a gene (aah) encoding L-alanine amide hydrolase using the cassette PCR method. Unless otherwise indicated specifically, the experiment was carried out based on the method described in the manual. In the cassette PCR method, in case of using Primer 1 (1st PCR, SEQ ID No.: 2) and Primer 2 (2nd PCR, SEQ ID No.: 3) as primers, a roughly 0.5 kilobase (kb) band (Fragment 1) was amplified with the Eco RI cassette. As a result of determining the base sequence of this fragment, Fragment 1 was verified to be a portion of aah.

5. Cloning of L-Alanine Amide Hydrolase Gene from Gene Library

In order to acquire the entire length of aah, Southern hybridization was carried out first using Fragment 1 as a probe.

The DNA fragment to serve as the probe was prepared to about 50 nanogram/microliters (ng/μl) and the probe was labeled by incubating 16 μl of this DNA solution at 37° C. for 24 hours in accordance with the protocol using DIG High Prime (Boehringer-Mannheim).

1 μg of chromosomal DNA was completely digested by combining various restrictases, electophoresed with 0.8% agarose gel, and then blotted onto Nylon membranes (Boehringer-Mannheim, positively charged Nylon membranes). Southern hybridization was then carried out in accordance with the established method. Hybridization was carried out using DIG Easy Hyb (Boehringer-Mannheim), and after hybridizing at 50° C. for 30 minutes, the probe was added following by hybridizing at 50° C. for 18 hours. Detection was carried out using the DIG Nucleotide Detection Kit (Boehringer-Mannheim).

As a result, a band was detected at about the 7 kb position in the Bgl II severed product. This 7 kb domain fragment was collected and coupled to pUC18 to produce a library (120 strains) with E. coli JM109. Colony hybridization was then carried out in accordance with the established methods. The colonies were then transferred to Nylon membrane filters (Boehringer-Mannheim, Nylon membranes for colony and plaque hybridization) followed by alkali denaturation, neutralization and immobilization treatment. Hybridization was carried out using DIG Easy Hyb. The filter was immersed in a buffer and pre-hybridized at 42° C. for 30 minutes. Subsequently, the aforementioned labeled probe was added, followed by hybridization at 42° C. for 18 hours. After washing with SSC buffer, one positive clone was selected using the DIG Nucleotide Detection Kit.

6. Base Sequence of L-Alanine Amide Hydrolase Gene Derived from *Corynebacterium glutamicum* Strain ATCC 13286

Plasmids retained by the selected transformant were prepared in accordance with the method described in Molecular Cloning, 2nd edition, Cold Spring Harbor Press (1989), and the base sequence in the vicinity that hybridized with the probe was determined. An open reading frame (ORF) was present that encoded protein containing 30 residues of the N-terminal amino acid sequence of L-alanine amide hydrolase, and was verified to be the gene aah that encodes L-alanine amide hydrolase. The base sequence of the full-length L-alanine amide hydrolase gene is shown in SEQ ID No.: 4 of the Sequence Listing. When the homology of the resulting ORF was examined using Genetyx, the base sequence exhibited a homology of 57.6% with the known proline iminopeptidase derived from *Propionibacterium* bacteria.

Example 8

Expression of L-Alanine Amide Hydrolase Gene in *E. coli*

Plasmid pUCAAH coupled to aah downstream of the lac promoter of pUC18 was constructed in order to express aah in *E. coli*. Fragments amplified by PCR using the chromosomal DNA of *Corynebacterium glutamicum* strain ATCC 13286 as template and the oligonucleotides shown in Table 4 as primers were treated with Sac I and Sma I, and after ligating to the Sac I- and Sma I-cleaved product of pUC18, were used to transform *E. coli* JM109. Strains having the target plasmid were selected from ampicillin-resistant strains, and the constructed expression plasmid was designated as pUCAAH.

TABLE 4

Primers Used to Construct L-Alanine Amide Hydrolase Expression Vector

| Primer | Sequence |
| --- | --- |
| 5' side | GGCGAGCTCGGGCAGTGGTGGGGGTGGTGT<br>Sac I<br>(SEQ ID No.: 6) |
| 3' side | CGGGGGCCCTCAGCGTACCTCTCGGCCGTG<br>Sma I<br>(SEQ ID No.: 7) |

The transformant expressing L-alanine amide hydrolase in *E. coli* having pUCAAH was seed cultured at 37° C. for 16 hours in LB medium containing 0.1 mg/ml ampicillin. 1 ml of this pre-culture liquid was seeded into a 500 ml Sakaguchi flask containing 50 ml of LB medium followed by final culturing at 37° C. Two hours after the start of culturing, isopropyl-1-thio-β-D-galactopyranoside (IPTG) was added to a final concentration of 1 mM followed by additionally culturing for 3 hours. Following completion of the culturing, the microbes were collected and washed, suspended in 10 ml of 20 mM phosphate buffer (pH 8.0), and then subjected to ultrasonic crushing for 30 minutes at 180 W. The solution was recovered and centrifuged for 10 minutes at 12,000 rpm, and the resulting supernatant was used as a cell-free extract.

Example 9

Measurement of Activity of L-Alanine Amide Hydrolase

After completion of the culturing, a cell-free extract was prepared and the activity of L-alanine amide hydrolase was measured using this as the enzyme source. Measurement of L-alanine amide enzyme activity was carried out by incubating a reaction mixture containing 50 mM L-alanine amide, 150 mM L-glutamine, 100 mM Tris-HCl buffer (pH 9.0), 10 mM EDTA and enzyme solution at 30° C. for 60 minutes followed by stopping the reaction by adding aqueous phosphoric acid (pH 1.5) equal to four volumes of the reaction mixture. The amount of L-alanyl-L-glutamine was determined by HPLC. For the unit of enzyme activity, enzyme activity that produces 1 μmol of L-alanyl-L-glutamine in 1 minute under these conditions was defined as 1 unit (U).

The conditions of HPLC used for analysis were as indicated below.

Column: Inertsil ODS-2
Mobile phase: (aqueous phosphoric acid solution (pH 2.1)), 2.5 mM sodium-1-octanesulfonate/methanol=10/1
Column temperature: 40° C.
Flow rate: 1.0 ml/minute
Detection: UV, 210 nm As a result, 0.05 U/mg of L-alanine amide hydrolase activity was detected in the case of inserting pUC18 AAH, thereby confirming that the cloned aah gene was expressed in *E. coli*. Furthermore, no activity was detected when only pUC18 was inserted as a control.

Example 10

Expression of His-Tag L-Alanine Amide Hydrolase Gene in *E. coli*

Plasmid pQEAAH that expresses L-alanine amide hydrolase as an His-Taq protein downstream of the lac promoter of pUC18 was constructed to express aah in *E. coli*. Fragments amplified by PCR using the chromosomal DNA of *Corynebacterium glutamicum* strain ATCC 13286 as template and the oligonucleotides shown in Table 5 as primers were treated with Sac I and Sma I, and ligated to the Sac I- and Sma I-cleaved products of pQE-30 (Qiagen), and the resultant was used to transform *E. coli* JM109. Strains having the target plasmid were selected from ampicillin-resistant strains, and the constructed expression plasmid was designated as pQEAAH.

TABLE 5

Primers Used to Construct His-Tag L-Alanine Amide Hydrolase Expression Vector

| Primer | Sequence |
|---|---|
| 5' side | GGC <u>GAG CTC</u> ATG ACT AAA ACA CTT GGT TCC<br>Sac I<br>(SEQ ID No.: 8) |
| 3' side | CGG <u>GGG CCC</u> TCA GCG TAC CTC TCG GCC GTG<br>Sma I<br>(SEQ ID No.: 7) |

When the activity of the transformant expressing L-alanine amide hydrolase in *E. coli* having pQEAAH was measured in the same manner as previously described, it was found to exhibit L-alanine amide hydrolase activity of 0.48 U/mg.

Example 11

Preparation of His-Tag Purified Enzyme

Microbial cells from 150 ml of culture broth of *E. coli* JM109 having pQEAAH were crushed according to the aforementioned method, and an His-Tag L-alanine amide hydrolase was purified using the His Trap Kit (manufactured by Amersham Pharmacia Biotech) according to the protocol provided with the kit. 24 milligrams (mg) of protein was acquired that exhibited a single band on SDS-PAGE, and the specific activity of the L-alanine amide hydrolase of that protein was 13.4 U/mg. The production yield of Ala-Gln was 7.2% relative to L-alanine amide.

Example 12

Study of Substrate Specificity Using His-Tag Purified Enzyme

The synthesis of peptides other than the L-alanyl-L-asparagine and L-alanyl-L-glutamine indicated in Example 6 by the acquired L-alanine amide hydrolase was studied using His-Tag purified enzyme.

(1) Peptide Synthesis of L-Alanine Amide and Other L-Amino Acids

The synthesis reaction was carried out by incubating a reaction mixture containing 100 mM L-alanine amide, 150 mM test amino acid, 100 mM Tris-HCl buffer (pH 9.0), 10 mM EDTA and enzyme solution (0.0045 U/ml) at 25° C. for 3 hours followed by quantification of the peptides produced by HPLC. As a result, numerous other peptides were produced as indicated below in addition to L-alanyl-L-asparagine and L-alanyl-L-glutamine. 7.54 mM L-alanyl-glycine was synthesized in the case of using glycine for the test amino acid, 10.11 mM L-alanyl-L-alanine was synthesized in the case of using L-alanine, 9.72 mM L-alanyl-L-valine was synthesized in the case of using L-valine, 9.60 mM L-alanyl-L-leucine was synthesized in the case of using L-leucine, 14.11 mM L-alanyl-L-isoleucine was synthesized in the case of using L-isoleucine, 14.49 mM L-alanyl-L-methionine was synthesized in the case of using L-methionine, 0.81 mM L-alanyl-L-proline was synthesized in the case of using L-proline, 13.42 mM L-alanyl-L-phenylalanine was synthesized in the case of using L-phenylalanine, 10.09 mM L-alanyl-L-tryptophan was synthesized in the case of using L-tryptophan, 24.67 mM L-alanyl-L-serine was synthesized in the case of using L-serine, 20.76 mM L-alanyl-L-threonine was synthesized in the case of using L-threonine, 1.52 mM L-alanyl-L-tyrosine was synthesized in the case of using L-tyrosine, 18.83 mM L-alanyl-L-lysine was synthesized in the case of using L-lysine, 27.69 mM L-alanyl-L-arginine was synthesized in the case of using L-arginine, 12.52 mM L-alanyl-L-histidine was synthesized in the case of using L-histidine, and 1.20 mM L-alanyl-L-glutamate was synthesized in the case of using L-glutamic acid.

(2) Peptide Synthesis from Other L-Amino Acids and L-Glutamine

Peptide synthesis was carried out using glycine amide and L-aspartate-α-amide instead of L-alanine amide.

The synthesis reaction was carried out by incubating a reaction mixture containing 100 mM test amino acid amide, 150 mM L-glutamine, 100 mM Tris-HCl buffer (pH 9.0), 10 mM EDTA and enzyme (0.0045 U/ml) at 25° C. for 3 hours, followed by quantification of the peptides produced by HPLC. As a result, 17.7 mM glycyl-L-glutamine was produced in the case of using glycine amide. In addition, 21.2 mM α-L-aspartyl-glutamine was produced in the case of using L-aspartate-α-amide.

As has been described above, it was clearly demonstrated that the L-alanine amide hydrolase obtained in the manner previously described was able to use various types of L-amino acid amides and L-amino acids as substrates. Consequently, it was clearly determined that the resulting enzyme is more appropriately referred to as an L-amino acid amide hydrolase rather than an L-alanine amide hydrolase.

[Sequence Listing]

SEQ ID No.: 1: N-terminal amino acid sequence of L-alanine amide hydrolase derived from *Corynebacterium glutamicum*
SEQ ID No.: 2: PCR primer
SEQ ID No.: 3: PCR primer
SEQ ID No.: 4: CDS sequence of L-amino acid amide hydrolase derived from *Corynebacterium glutamicum*
SEQ ID No.: 5: Amino acid sequence of L-amino acid amide hydrolase derived from *Corynebacterium glutamicum*
SEQ ID No.: 6: Primer
SEQ ID No.: 7: Primer
SEQ ID No.: 8: Primer

INDUSTRIAL APPLICABILITY

According to the dipeptide production method of the present invention, a dipeptide can be produced using comparatively inexpensively available L-amino acid amide and L-amino acid without going through a complex synthesis method. This makes it possible to reduce the production cost of dipeptides useful as pharmaceutical materials, functional foods and so forth. In addition, according to the dipeptide production method of the present invention, various types of dipeptides can be produced using various types of L-amino acid amides and L-amino acids as raw materials. In addition, the L-amino acid amide hydrolase of the present invention can be advantageously used in the dipeptide production method of the present invention.

The invention claimed is:

1. A dipeptide production method comprising: producing a dipeptide from an L-amino acid amide and an L-amino acid using an enzyme or enzyme-containing substance having an L-amino acid amide hydrolase activity.

2. The dipeptide production method according to claim 1, wherein the enzyme or enzyme-containing substance is one or more types selected from the group consisting of a culture of microbes having an L-amino acid amide hydrolase activity, microbial cells separated from the culture, and a treated microbial cell product from the microbes.

3. The dipeptide production method according to claim 2, wherein the microbe belongs to the genus *Bacillus*, genus *Corynebacterium*, genus *Erwinia*, genus *Rhodococcus*, genus *Chryseobacterium*, genus *Micrococcus*, genus *Pseudomonas*, genus *Cryptococcus*, genus *Trichosporon*, genus *Rhodosporidium*, genus *Sporobolomyces*, genus *Tremela*, genus *Torulaspora*, genus *Sterigmatomyces* or genus *Rhodotorula*.

4. The dipeptide production method according to claim 1, wherein the enzyme is a protein (A) or (B):
   (A) a protein having the amino acid sequence described in SEQ ID NO: 5 of the Sequence Listing; and
   (B) a protein having an amino acid sequence that contains a substitution, deletion, insertion, addition or inversion of one or a plurality of amino acids in the amino acid sequence described in SEQ ID NO: 5 of the Sequence Listing, and having an L-amino acid amide hydrolase activity that catalyzes a reaction that produces a dipeptide from the L-amino acid amide and the L-amino acid.

5. The dipeptide production method according to claim 1, wherein the enzyme is a protein encoded by:
   a DNA that hybridizes under highly stringent conditions with a polynucleotide that consists of a base sequence complementary to the base sequence of bases nos. 57 to 1295 described in SEQ ID NO: 4 of the Sequence Listing, and encodes a protein having an L-amino acid amide hydrolase activity that catalyzes a reaction that produces a dipeptide from the L-amino acid amide and the L-amino acid.

6. The dipeptide production method according to claim 2, wherein the microbe is a microbe that has been transformed so as to be able to express a protein (A), (B) or (C):
   (A) a protein having the amino acid sequence described in SEQ ID No.: 5 of the Sequence Listing;
   (B) a protein having an amino acid sequence that contains a substitution, deletion, insertion, addition or inversion of one or a plurality of amino acids in the amino acid sequence described in SEQ ID NO: 5 of the Sequence Listing, and having an L-amino acid amide hydrolase activity that catalyzes a reaction that produces a dipeptide from the L-amino acid amide and the L-amino acid; and
   (C) a protein encoded by a DNA that hybridizes under highly stringent conditions with a polynucleotide that consists of a base sequence complementary to the base sequence of base nos. 57 to 1295 described in SEQ ID NO.: 4 of the Sequence Listing, and encodes a protein having an L-amino acid amide hydrolase activity that catalyzes a reaction that produces a dipeptide from the L-amino acid amide and the L-amino acid.

7. The dipeptide production method according to claim 1, wherein the L-amino acid amide is one or more types selected from the group consisting of L-alanine amide, glycine amide and L-aspartic acid-α-amide.

8. The dipeptide production method according to claim 1, wherein the L-amino acid is one or more types selected from the group consisting of L-glutamine, L-asparagine, glycine, L-alanine, L-valine, L-leucine, L-isoleucine, L-methionine, L-proline, L-phenylalanine, L-tryptophan, L-serine, L-threonine, L-tyrosine, L-lysine, L-arginine, L-histidine and L-glutamine.

9. A production method of L-amino acid amide hydrolase, comprising:
   culturing in a meduim a microbe transformed so as to be able to express a protein (A), (B) or (C): in cells of said microbe
   (A) a protein having the amino acid sequence described in SEQ ID No.: 5 of the Sequence Listing;
   (B) a protein having an amino acid sequence that contains a substitution, deletion, insertion, addition or inversion of one or a plurality of amino acids in the amino acid sequence described in SEQ ID No.: 5 of the Sequence Listing, and having an L-amino acid amide hydrolase activity that catalyzes a reaction that produces a dipeptide from the L-amino acid amide and the L-amino acid; and
   (C) a protein encoded by a DNA that hybridizes under stringent conditions with a polynucleotide that consists of a base sequence complementary to the base sequence of bases nos. 57 to 1295 described in SEQ ID No.: 4 of the Sequence Listing, and encodes a protein having an L-amino acid amide hydrolase activity that catalyzes a reaction that produces a dipeptide from the L-amino acid amide and the L-amino acid, and accumulating in the medium and/or cells an L-amino acid amide hydrolase that catalyzes a reaction that produces a dipeptide from an L-amino acid amide and an L-amino acid.

* * * * *

SEQUENCE LISTING

```
<160> NUMBER OF SEQ ID NOS: 8

<210> SEQ ID NO 1
<211> LENGTH: 30
<212> TYPE: PRT
<213> ORGANISM: Corynebacterium glutamicum
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 1

Thr Lys Thr Leu Gly Ser Leu Gln Leu Glu Glu Ile Thr Leu Thr Leu
1               5                   10                  15

Pro Leu Thr Glu Asp Val Ala Asp Glu Xaa Arg Xaa Glu Xaa
            20                  25                  30

<210> SEQ ID NO 2
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n is a, c, g, or t

<400> SEQUENCE: 2
gghwsnytbc arytbgarga ratyac                                          26

<210> SEQ ID NO 3
<211> LENGTH: 27
<212> TYPE: DNA
<213> ORGANISM: Artificial Sequence
<220> FEATURE:
```

<223> OTHER INFORMATION: Synthetic DNA

<400> SEQUENCE: 3
carytbgarg aratyacbyt bacbytb        27

<210> SEQ ID NO 4
<211> LENGTH: 1307
<212> TYPE: DNA
<213> ORGANISM: Corynebacterium glutamicum
<220> FEATURE:
<221> NAME/KEY: CDS
<222> LOCATION: (57)..(1295)

<400> SEQUENCE: 4

```
ggcgagctcg ggcagtggtg ggggtggtgt ccaccccctgc gcgtaacctg ggaagc atg     59
                                                              Met
                                                                1 act aaa aca ctt ggt tcc ctt caa ctt gaa gaa att acc ttg acg ctc        107
Thr Lys Thr Leu Gly Ser Leu Gln Leu Glu Glu Ile Thr Leu Thr Leu
          5                  10                  15 cct ctg act gaa gat gtg gcc gat gaa cgc acc att gat gtg ttc gca       155
Pro Leu Thr Glu Asp Val Ala Asp Glu Arg Thr Ile Asp Val Phe Ala
     20                  25                  30 cgc att gcc aca cgc gtc ggt ggg gaa gac ctt cca tat tta gta ttc       203
Arg Ile Ala Thr Arg Val Gly Gly Glu Asp Leu Pro Tyr Leu Val Phe
 35                  40                  45 ctg cag ggt ggg cct ggc aat gaa gct cca cgt cca agc ctt aat ccc       251
Leu Gln Gly Gly Pro Gly Asn Glu Ala Pro Arg Pro Ser Leu Asn Pro
 50                  55                  60                  65 ctc aac ccc aat tgg ttg ggc gtg gcc ttg gag gaa tac cgc gtg gtc       299
Leu Asn Pro Asn Trp Leu Gly Val Ala Leu Glu Glu Tyr Arg Val Val
                 70                  75                  80 atg ttg gat caa cgt ggc acc ggc cgt tcc acc cca gtg ggt aat gat       347
Met Leu Asp Gln Arg Gly Thr Gly Arg Ser Thr Pro Val Gly Asn Asp
             85                  90                  95 att ttg gaa aaa ccc aca gca gaa gta gtg gag tac tta tcc cac ctg       395
Ile Leu Glu Lys Pro Thr Ala Glu Val Val Glu Tyr Leu Ser His Leu
        100                 105                 110 cgc gca gat ggc att gtg cga gat gct gaa gcc ctg cgt aag cat ttg       443
Arg Ala Asp Gly Ile Val Arg Asp Ala Glu Ala Leu Arg Lys His Leu
    115                 120                 125 ggt gtg aat cag tgg aac ctt tta ggc cag tcc ttc gga ggt ttc acc       491
Gly Val Asn Gln Trp Asn Leu Leu Gly Gln Ser Phe Gly Gly Phe Thr
130                 135                 140                 145 acc ctg cat tac ttg tcc cgg cac gcc gat tcc ttg gac aac gtg ttt       539
Thr Leu His Tyr Leu Ser Arg His Ala Asp Ser Leu Asp Asn Val Phe
                150                 155                 160 att acc ggc ggt ctc agc gct att gat cgc cca gca gaa gac gtg tat       587
Ile Thr Gly Gly Leu Ser Ala Ile Asp Arg Pro Ala Glu Asp Val Tyr
            165                 170                 175 gcc aac tgt tac aac cgc atg cgc cga aac tct gag gaa ttc tac cgt       635
Ala Asn Cys Tyr Asn Arg Met Arg Arg Asn Ser Glu Glu Phe Tyr Arg
        180                 185                 190 cgc ttc ccg caa tta cgg gaa act ttc cga ggg ttg gtt aat cgt gct       683
Arg Phe Pro Gln Leu Arg Glu Thr Phe Arg Gly Leu Val Asn Arg Ala
    195                 200                 205 cgc gcc ggg gag att gtg ctt ccc acc ggc gaa gtt gtg tca gaa acc       731
Arg Ala Gly Glu Ile Val Leu Pro Thr Gly Glu Val Val Ser Glu Thr
210                 215                 220                 225 agg ctg cga tcc ctt ggt cac ttg ttg ggt agc aat gac ggc tgg ttt       779
Arg Leu Arg Ser Leu Gly His Leu Leu Gly Ser Asn Asp Gly Trp Phe
```

```
                    230                 235                 240
gat ctg tac aac ctg ctg gaa tta gat ccc acc tcc aac gct ttt gtc    827
Asp Leu Tyr Asn Leu Leu Glu Leu Asp Pro Thr Ser Asn Ala Phe Val
            245                 250                 255 cat gac ctg gca gga ctt ttg cct ttc ggc aac cgc aac cca att tat    875
His Asp Leu Ala Gly Leu Leu Pro Phe Gly Asn Arg Asn Pro Ile Tyr
        260                 265                 270 tac gtg ctc cat gag tcc tct tac gcc gac ggt gtg gtg aca aat tgg    923
Tyr Val Leu His Glu Ser Ser Tyr Ala Asp Gly Val Val Thr Asn Trp
    275                 280                 285 gca gca gag cgt gtg ctt cca gag gat ttc cgc gag gat cca aca ctg    971
Ala Ala Glu Arg Val Leu Pro Glu Asp Phe Arg Glu Asp Pro Thr Leu
290                 295                 300                 305 ctc acc ggt gag cac gtg ttc cag gag tgg aca gac acc gtg ccg tcg   1019
Leu Thr Gly Glu His Val Phe Gln Glu Trp Thr Asp Thr Val Pro Ser
            310                 315                 320 ctc aag ccg tgg aag gac gtt gcc ctg gca ttg gct cag cag gaa tgg   1067
Leu Lys Pro Trp Lys Asp Val Ala Leu Ala Leu Ala Gln Gln Glu Trp
        325                 330                 335 ccc aag ctt tat gat gcg aag gca ttg gaa aac tca cag gcc aag ggc   1115
Pro Lys Leu Tyr Asp Ala Lys Ala Leu Glu Asn Ser Gln Ala Lys Gly
    340                 345                 350 gct gca gca gtg tat ghc aat gac gtt ttc gtc cca gtg gat tac tct   1163
Ala Ala Ala Val Tyr Xaa Asn Asp Val Phe Val Pro Val Asp Tyr Ser
355                 360                 365 ctg gaa acc gca caa cac ctg ccc ggt gtg cag ctg ttt atc acc agc   1211
Leu Glu Thr Ala Gln His Leu Pro Gly Val Gln Leu Phe Ile Thr Ser
370                 375                 380                 385 cag cat gaa cac aat gga ctt cgt gcc agc tca ggc gca gta ctg rag   1259
Gln His Glu His Asn Gly Leu Arg Ala Ser Ser Gly Ala Val Leu Xaa
            390                 395                 400 cac ctt ttc gat ctg gcc cac ggc cga gag gta cgc tgagggcccc cg     1307
His Leu Phe Asp Leu Ala His Gly Arg Glu Val Arg
        405                 410

<210> SEQ ID NO 5
<211> LENGTH: 413
<212> TYPE: PRT
<213> ORGANISM: Corynebacterium glutamicum
<220> FEATURE:
<221> NAME/KEY: misc_feature
<222> LOCATION: (359)..(359)
<223> OTHER INFORMATION: The 'Xaa' at location 359 stands for Asp, Ala,
      or Val.
<220> FEATURE:
<221> NAME/KEY: misc_feature
<222> LOCATION: (401)..(401)
<223> OTHER INFORMATION: The 'Xaa' at location 401 stands for Glu, or
      Lys.

<400> SEQUENCE: 5

Met Thr Lys Thr Leu Gly Ser Leu Gln Leu Glu Glu Ile Thr Leu Thr
1               5                   10                  15

Leu Pro Leu Thr Glu Asp Val Ala Asp Glu Arg Thr Ile Asp Val Phe
            20                  25                  30

Ala Arg Ile Ala Thr Arg Val Gly Gly Glu Asp Leu Pro Tyr Leu Val
        35                  40                  45

Phe Leu Gln Gly Gly Pro Gly Asn Glu Ala Pro Arg Pro Ser Leu Asn
    50                  55                  60

Pro Leu Asn Pro Asn Trp Leu Gly Val Ala Leu Glu Glu Tyr Arg Val
65                  70                  75                  80
```

```
Val Met Leu Asp Gln Arg Gly Thr Gly Arg Ser Thr Pro Val Gly Asn
             85                  90                  95

Asp Ile Leu Glu Lys Pro Thr Ala Glu Val Val Glu Tyr Leu Ser His
            100                 105                 110

Leu Arg Ala Asp Gly Ile Val Arg Asp Ala Glu Ala Leu Arg Lys His
            115                 120                 125

Leu Gly Val Asn Gln Trp Asn Leu Leu Gly Gln Ser Phe Gly Gly Phe
        130                 135                 140

Thr Thr Leu His Tyr Leu Ser Arg His Ala Asp Ser Leu Asp Asn Val
145                 150                 155                 160

Phe Ile Thr Gly Gly Leu Ser Ala Ile Asp Arg Pro Ala Glu Asp Val
                165                 170                 175

Tyr Ala Asn Cys Tyr Asn Arg Met Arg Arg Asn Ser Glu Glu Phe Tyr
            180                 185                 190

Arg Arg Phe Pro Gln Leu Arg Glu Thr Phe Arg Gly Leu Val Asn Arg
        195                 200                 205

Ala Arg Ala Gly Glu Ile Val Leu Pro Thr Gly Glu Val Val Ser Glu
    210                 215                 220

Thr Arg Leu Arg Ser Leu Gly His Leu Leu Gly Ser Asn Asp Gly Trp
225                 230                 235                 240

Phe Asp Leu Tyr Asn Leu Leu Glu Leu Asp Pro Thr Ser Asn Ala Phe
                245                 250                 255

Val His Asp Leu Ala Gly Leu Leu Pro Phe Gly Asn Arg Asn Pro Ile
            260                 265                 270

Tyr Tyr Val Leu His Glu Ser Ser Tyr Ala Asp Gly Val Val Thr Asn
        275                 280                 285

Trp Ala Ala Glu Arg Val Leu Pro Glu Asp Phe Arg Glu Asp Pro Thr
    290                 295                 300

Leu Leu Thr Gly Glu His Val Phe Gln Glu Trp Thr Asp Thr Val Pro
305                 310                 315                 320

Ser Leu Lys Pro Trp Lys Asp Val Ala Leu Ala Leu Ala Gln Gln Glu
                325                 330                 335

Trp Pro Lys Leu Tyr Asp Ala Lys Ala Leu Glu Asn Ser Gln Ala Lys
            340                 345                 350

Gly Ala Ala Val Tyr Xaa Asn Asp Val Phe Val Pro Val Asp Tyr
        355                 360                 365

Ser Leu Glu Thr Ala Gln His Leu Pro Gly Val Gln Leu Phe Ile Thr
    370                 375                 380

Ser Gln His Glu His Asn Gly Leu Arg Ala Ser Ser Gly Ala Val Leu
385                 390                 395                 400

Xaa His Leu Phe Asp Leu Ala His Gly Arg Glu Val Arg
                405                 410
```

<210> SEQ ID NO 6
<211> LENGTH: 30
<212> TYPE: DNA
<213> ORGANISM: Artificial Sequence
<220> FEATURE:
<223> OTHER INFORMATION: Synthetic DNA

<400> SEQUENCE: 6
ggcgagctcg ggcagtggtg ggggtggtgt                              30

<210> SEQ ID NO 7
<211> LENGTH: 30
<212> TYPE: DNA

-continued

```
<213> ORGANISM: Artificial Sequence
<220> FEATURE:
<223> OTHER INFORMATION: Synthetic DNA

<400> SEQUENCE: 7 cggggggccct cagcgtacct ctcggccgtg                           30

<210> SEQ ID NO 8
<211> LENGTH: 30
<212> TYPE: DNA
<213> ORGANISM: Artificial Sequence
<220> FEATURE:
<223> OTHER INFORMATION: Synthetic DNA

<400> SEQUENCE: 8
ggcgagctca tgactaaaac acttggttcc                            30
```